(12) United States Patent
Bernatek et al.

(10) Patent No.: US 6,466,313 B1
(45) Date of Patent: Oct. 15, 2002

(54) METHOD AND APPARATUS FOR DETERMINING THE TIME CURVE OF THE INTENSITY OF RADIATION IN A WEATHERING TESTING DEVICE

(75) Inventors: Christian Bernatek, Rodgau; Bernd Rudolph, Alzanau, both of (DE)

(73) Assignee: Atlas Material Testing Technology GmbH, Linsengericht/Altenhasslau (DE)

( * ) Notice: Subject to any disclaimer, the term of this patent is extended or adjusted under 35 U.S.C. 154(b) by 0 days.

(21) Appl. No.: 09/485,333
(22) PCT Filed: Aug. 4, 1998
(86) PCT No.: PCT/EP98/04855
§ 371 (c)(1), (2), (4) Date: Aug. 14, 2000
(87) PCT Pub. No.: WO99/10727
PCT Pub. Date: Mar. 4, 1999

(30) Foreign Application Priority Data

Aug. 6, 1997 (DE) .......................................... 197 33 957

(51) Int. Cl.⁷ ............................. G01J 1/00; G01N 17/00
(52) U.S. Cl. ........................ 356/226; 250/372; 356/51; 73/150 R
(58) Field of Search .......................... 356/51, 218, 226; 250/372; 73/150 R

(56) References Cited

U.S. PATENT DOCUMENTS

| 4,391,522 A | 7/1983 | Schmid et al. ............... 356/326 |
| 4,618,776 A | 10/1986 | Stürm et al. ................. 250/372 |

FOREIGN PATENT DOCUMENTS

| DE | 29 40 325 | 4/1981 |
| DE | 33 10 631 | 10/1984 |

*Primary Examiner*—F. L. Evans
(74) *Attorney, Agent, or Firm*—Cohen, Pontani, Lieberman & Pavane

(57) ABSTRACT

A method for determining the time curve of the intensity of radiation present at the location of at least one sample which is being examined. The sample follows a circular path of movement in a sealed sample chamber of a weathering testing device, around a stationary radiation device for producing UW and global radiation. At least one sensor which detects the momentary radiation intensity of the radiation device is provided. The sensor moves together with the at least one sample, and is displaced in relation thereto in relation to the radiation device, for example in the peripheral direction of the path of movement. An electrical signal corresponding to the momentary intensity of the radiation is derived by the sensor at set intervals.

16 Claims, 3 Drawing Sheets

METHOD AND APPARATUS FOR DETERMINING THE TIME CURVE OF THE INTENSITY OF RADIATION IN A WEATHERING TESTING DEVICE

FIELD OF THE INVENTION

The invention relates to a method for determining the course over time of the radiation intensity at the location of at least one sample to be examined, which moves in an enclosed sample chamber of a weathering testing device over a circular path of motion about a stationary radiation device for generating UV and global radiation, having at least one sensor detecting the instantaneous radiation intensity of the radiation device, which sensor, together with the at least one sample and offset from it relative to the radiation device, for example offset in the circumferential direction of the path of motion, moves substantially along the path of motion, and an electrical measurement signal corresponding to the instantaneous radiation intensity is derived by the sensor at intervals over time. The invention also relates to a device used to perform this method.

BACKGROUND OF THE INVENTION

Weathering testing devices are used to test the lightfastness and aging of arbitrary samples, which are distributed over a circular path of motion in the enclosed sample chamber and move around the stationary radiation device. Rain bars or other stationary equipment elements can also be provided in the weathering testing device to allow examination of specimens taking the required ambient conditions into account. As a result, the radiation path from the radiation device to the samples and to the sensor moved along with the samples is repeatedly interrupted or interfered with by stationary obstacles presented by the equipment. In the known devices, the course over time of the radiation intensity is ascertained by making practically individual snapshots of the radiation intensity at comparatively long time intervals or at isolated circumferential positions along the path of motion. It is accordingly impossible to estimate how the equipment-dictated unavoidable interruptions of radiation will affect the measurement error in detecting the radiation intensity. Accordingly it is certainly possible that the radiation interruptions will repeatedly arrive at unfavorable rotational positions of the sensor around the radiation device, causing considerable measurement error with regard to the radiation sent to the samples.

SUMMARY OF THE INVENTION

The object of the present invention is to embody a method and a device of the generic type in question such that while avoiding the above disadvantages, more-reliable detection of the course over time of the radiation intensity at the location of the sample is possible. Individual stationary obstacles presented by the equipment to the radiation should have practically no further effect of adulterating the outcome. The method should also be well-suited to industrial realization using current- or energy-saving circuit components, such as for battery and rechargeable battery operation of a device functioning accordingly.

For attaining this object, the measurement signal is integrated in analog fashion in accordance with a first, adjustable timing code with relatively short code intervals at least once in each of these short code intervals via a certain integration interval of adjustable chronological length; that the thus-obtained analog-integrated measurement values of each short code interval are digitized; that the digitized measurement values of a plurality of successive code intervals of the first timing code are arithmetically added and averaged in accordance with a second, adjustable timing code with comparatively longer code intervals, in each of these longer code intervals; and that the thus-obtained arithmetically added, averaged measurement values are stored in memory digitally in a manner capable of chronological association and capable of being called up.

In this method, the influence of individual stationary obstacles to radiation presented by the equipment on the outcome of measurement is practically precluded, since in the analog integration operations, repeated at rapid time intervals, with chronologically long-lasting integration intervals and ensuing addition and averaging of a plurality of individual outcomes, instantaneous situations unfavorable from a radiation standpoint are dropped from the outcome or practically fail to arise. Because of the relatively brief integration intervals with ensuing digitization and digital further processing and storage in memory, the method is very well-suited for a relatively simple, inexpensive practical embodiment, such as for battery and rechargeable battery operation, and thus for mobile use of suitably operating devices using economical circuit components available on the market. Furthermore, for non- battery operation, the influence of possible fluctuations or breakdowns in mains voltage on the outcome of measurement is largely suppressed.

Only the arithmetically added and averaged measurement values are stored in memory for longer, the course over time of the radiation intensity can also be detected over a longer period of time without major expense for memory.

The particularly randomly controlled shifting of the integration intervals lead to a further improvement in the reliability of the method, since the influence of existing interference variables that have the same effect and are thus added together is avoided even more. This is true both for the influence of obstacles to radiation and the influence of mains disruptions.

To attain the stated object, a device suitable for performing the method, is distinguished according to the invention by connecting to the output of the sensor 20, 22 a clocked analog integrator 26, which in analog fashion integrates the measurement signal, in accordance with a first, adjustable timing code with relatively short code intervals a at least once in each of these short code intervals, via a certain integration interval c of adjustable chronological length; display device 34. A microprocessor 36 controls the individual components of the device and can, as in the present case, be linked with an random generator 38.

This device, with a comparatively simple and inexpensive construction, allows easy practical realization of the method of the invention using structural components available on the market.

The timing pulses can be adjusted and adapted to applicable operating conditions. The clock generator always assures correctly timed operation of the individual components of the device that are affected by it. Thus the use of a microprocessor is proved to be especially favorable, especially since a microprocessor is both commercially available and inexpensive and operates in an energy-saving way. The microprocessor can then control the entire course of operation of the device.

One embodiment enables temporary, incrementally renewable storage in memory of information corresponding to the course over time of the radiation intensity.

The integration intervals can be shifted under random control to further suppress error.

BRIEF DESCRIPTION OF THE DRAWINGS

The invention will be described below in further detail in terms of exemplary embodiments shown in the drawings. Shown are.

DETAILED DESCRIPTION OF THE PREFERRED EMBODIMENT

Figure 1:
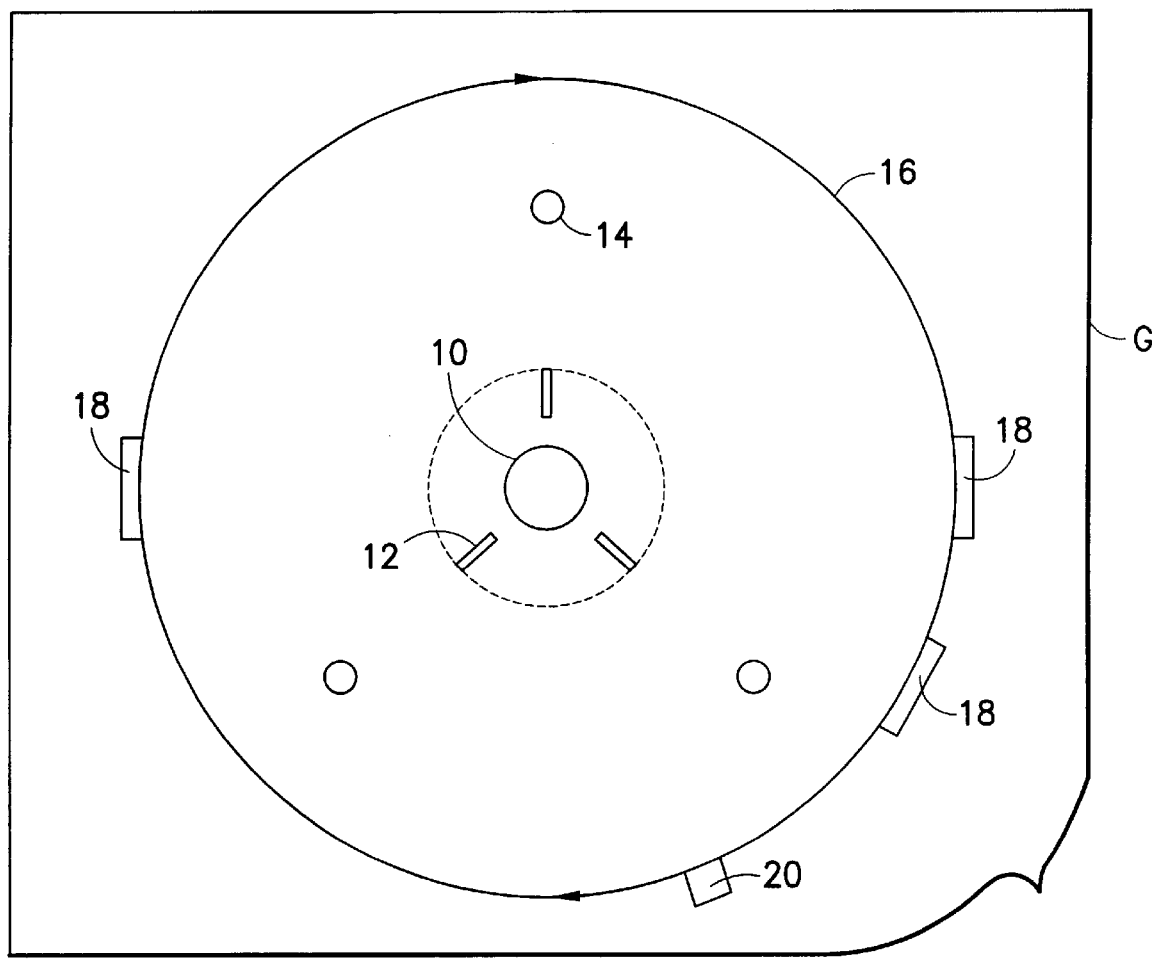
FIG. 1, in a schematic plan view, a weathering testing device with a device operating by the method of the invention.

In FIG. 1, a stationary radiation device 10 constructed in one or multiple parts, for generating UV and global radiation, is located in a closed housing G of a weathering testing device. The radiation device 10 is surrounded by stationary radiation-disrupting obstacles presented the equipment, such as absorber baffles 12, rain bars 14, and other mechanical parts of the equipment. A circular path of motion 16 extends around the radiation device 10, the latter being positioned centrally, for instance. Samples 18 to be examined, three of which are shown as examples, are guided in operation along the path of motion 16 around the radiation device 10 and acted upon by the radiation of the radiation device 10.

The course over time of the radiation intensity at the location of the sample to be examined is detected with at least one sensor 20 that reacts to the radiation of the radiation device 10. This sensor is likewise moved along the path of motion 16 together with the samples and in the present case is disposed offset in the circumferential direction from the samples 18. It could also be offset in height relative to the samples 18, instead, without any circumferential offset.

The stationary mechanical parts that intersect the beam path from the radiation device 10 to the samples 18 and also to the sensor 20 lead to unavoidable measurement errors. These errors can have extremely adverse effects, especially whenever the sensor 10 makes only brief snapshots of the radiation intensity at relatively long time intervals. In that case it can happen that repeatedly, the sensor 20 is in operation only in the radiation disrupting range. Mains disruptions can also repeatedly have adverse effects. To overcome these disadvantages, the device for performing the method is constructed as shown in FIG. 2.

Figure 2:
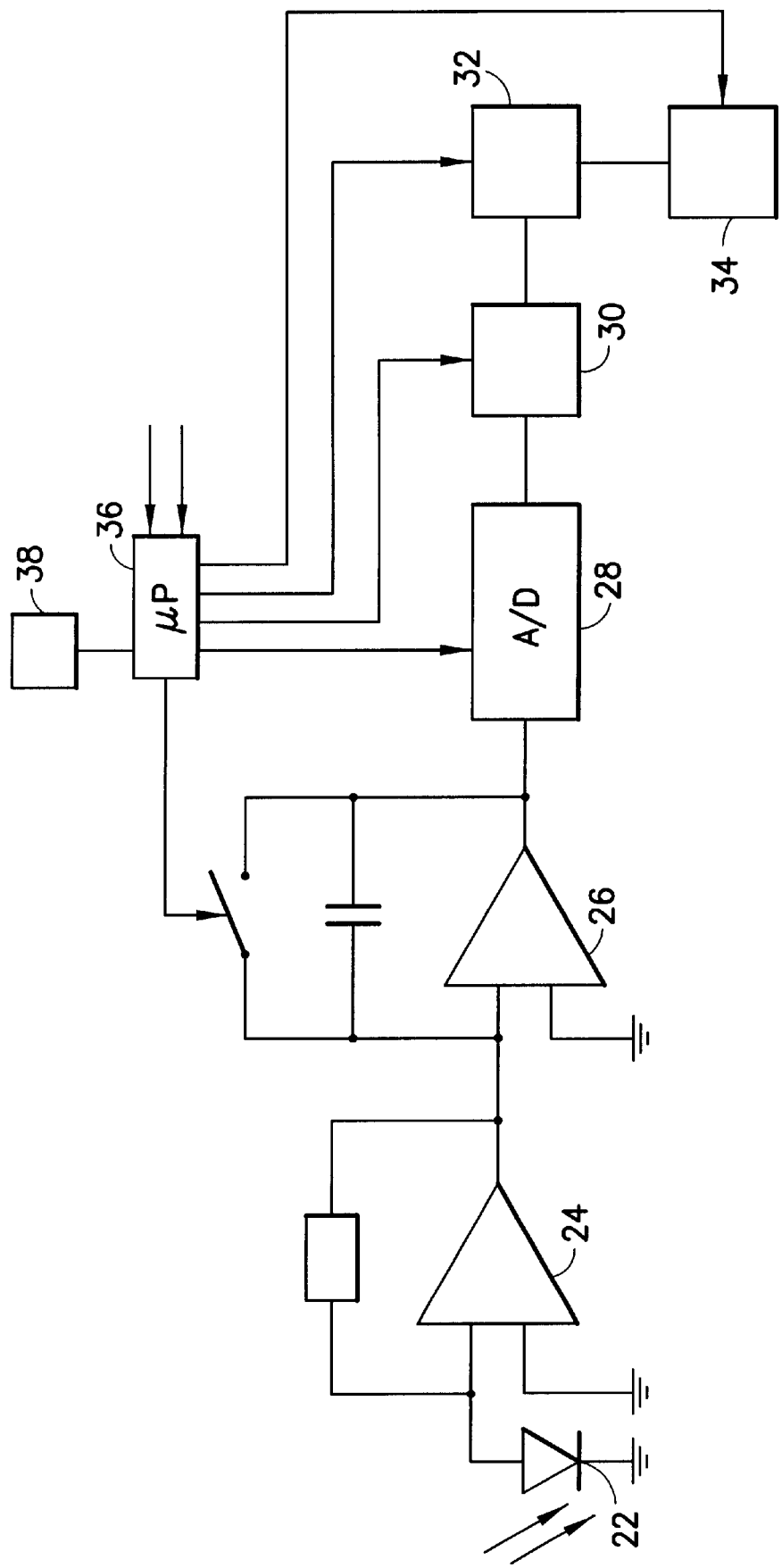
FIG. 2, in a schematic block circuit diagram, circuitry details of the device for performing the method of the invention.

In FIG. 2, as the sensor 20, a receiving diode 22 that is sensitive to the radiation of the radiation device 10 and is moved along the path of motion 16 is connected on the output side, via an amplifier 24, to a clocked integrator 26, which in turn is connected to an analog/digital converter 28. The output of the analog/digital converter is coupled to an averaging addition element 30, which is connected to a memory element 32. The contents of the memory can be shown on a display device 34. A microprocessor 36 controls the individual components of the device and can, as in the present case, be linked with a random generator 38.

The microprocessor 36, also functioning as a clock generator, generates a first adjustable timing code with relative short successive code intervals a, which in the example of FIG. 3 have a length of 1 second (or 0.5 seconds). It also generates even shorter integration intervals c, which in FIG. 3 have a length of 0.4 seconds, as an example. In FIG. 3, as an example, two integration intervals c of equal length per code interval a are generated, which are distributed without overlap and with mutual chronological spacing over the code interval a; in the example of FIG. 3, they end in the code interval a at 0.5 and 1.0 seconds.

During each integration interval c, the integrator 26 assures an analog integration of the measurement signal from the receiving diode 22. The measurement value of the integrator 26 that is available at the end of each integration interval c is digitized by the analog/digital converter 28. A train of the digitized values is shown schematically in FIG. 3B.

Figure 3A:
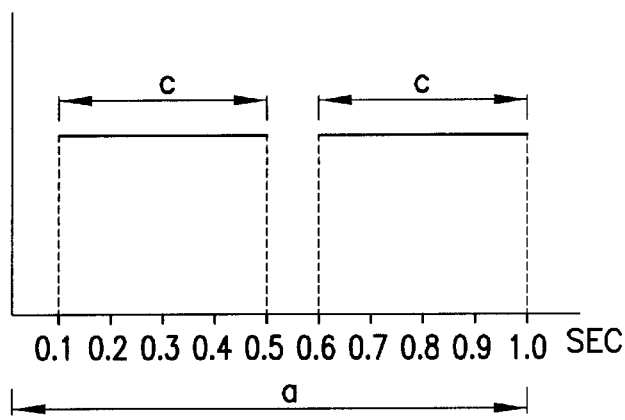
FIGS. 3A–3D, graphs for further exemplary explanation of the invention.
Figure 3B:
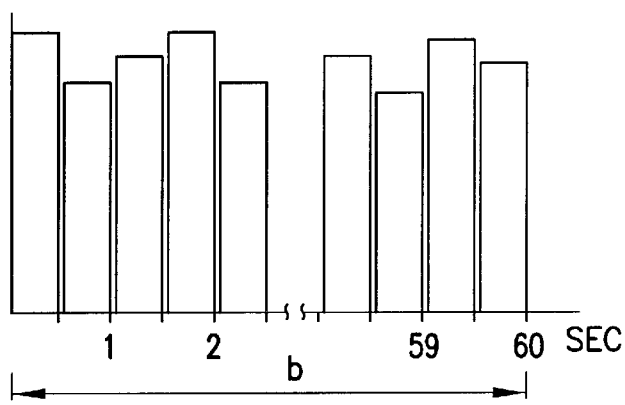
Figure 3C:
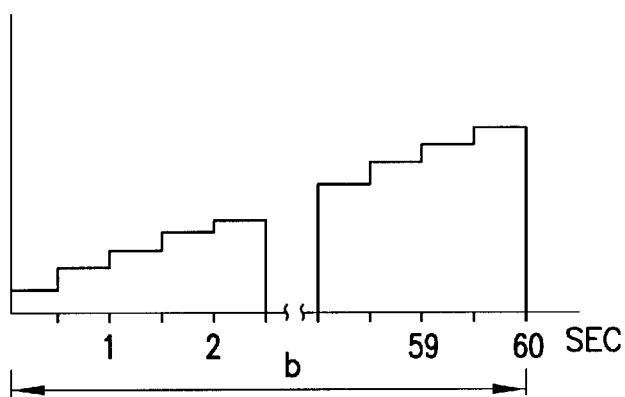

The microprocessor 36 also generates a second adjustable timing code with comparatively longer successive code intervals b, which in FIG. 3C have a length of 60 seconds, as an example. During each code interval b, the digitized measurement values belonging together from a plurality of successive code intervals a are arithmetically added up and averaged by the addition element 30. The arithmetical addition of the digitized values during the code interval b is shown schematically in FIG. 3C, represented symbolically by a stairstep curve.

Figure 3D:
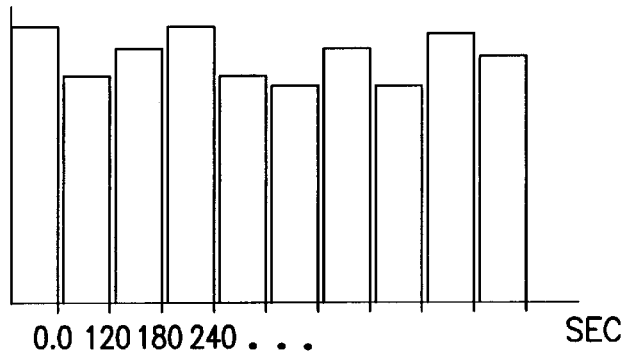

The measurement values output at the end of each of the code intervals b by the addition element 30 are stored in the memory element 34 in chronologically correct order and can thus be shown on the display device with correct timing. A limited number of the most recently occurring measurement values from the addition element 30 are shown in FIG. 3D and are stored in the memory element 32 at any given time. To that end, the memory element 32 is embodied as a shift register, for example, through which the measurement values run.

With the random generator, the position of the integration intervals c within the code intervals can be shifted under random control.

The device can be modified in manifold ways within the scope of the invention. For instance, the code intervals a, b of the timing codes and the number and position of the integration intervals c within the code intervals and the number of measurement values stored simultaneously in the memory element 32 at a given time can be adapted to the prevailing requirements at the time. The detailed technical layout of the equipment can also be modified in manifold ways.

What is claimed is:

1. A method for determining the course over time of the radiation intensity at the location of at least one sample to be examined, which moves in an enclosed sample chamber of a weathering testing device over a circular path of motion about a stationary radiation device for generating UV and global radiation, having at least one sensor detecting the instantaneous radiation intensity of the radiation device, which sensor, together with the at least one sample and offset from it relative to the radiation device, moves substantially along the path of motion, and an electrical measurement signal corresponding to the instantaneous radiation intensity is derived by the sensor at intervals over time, characterized in that the measurement signal is integrated in analog fashion in accordance with a first, adjustable timing code with relatively short code intervals at least once in each of these short code intervals via a certain integration interval of adjustable chronological length;

that the thus-obtained analog-integrated measurement values of each short code interval are digitized;

that the digitized measurement values of a plurality of successive code intervals of the first timing code are arithmetically added and averaged in accordance with a second, adjustable timing code with comparatively longer code intervals, in each of these longer code intervals; and that the thus-obtained arithmetically added, averaged measurement values are stored in memory digitally in such a manner that they can be chronologically ordered and can be called up.

2. The method of claim 1, characterized in that the arithmetically added, averaged measurement values are stored in memory such that they can be called up over an adjustable longer time period.

3. The method of claim 1, characterized in that the integration intervals are chronologically shifted within successive code intervals of the first timing code.

4. The method of claim 3, characterized in that the integration intervals are shifted chronologically irregularly, as if randomly controlled, within successive code intervals of the first timing code.

5. The method of claim 1, characterized in that the first timing code has constant code intervals of approximately 500 milliseconds; that per code interval, one integration interval with a length of approximately 200 to approximately 500 milliseconds is used; and that the second timing code has constant code intervals of approximately 60 seconds.

6. The method of claim 1, characterized in that the integration intervals of the first timing code each end at the end of respective constant code intervals.

7. The method of claim 1, characterized in that the integration intervals of the first timing code each begin at the beginning of respective constant code intervals.

8. The method of one of claim 1, characterized in that at least two integration intervals that do not overlap chronologically are used per code interval of the first timing code.

9. The method of claim 8, characterized in that the at least two integration intervals are of equal length.

10. The method of claim 8, characterized in that the at least two integration intervals are of different lengths, and that their total length is the same in all the code intervals of the first timing code.

11. The method of claim 1, characterized in that in addition to the radiation intensity, other measurement variables are detected in accordance with the radiation-dependent measurement signal and processed further.

12. A device for performing the method of claim 1, having at least one sensor detecting the instantaneous radiation intensity of the central radiation device, which sensor moves together with the at least one measurement sample and offset from it relative to the radiation device, over the circular path of motion, and an electrical measurement signal corresponding to the instantaneous radiation intensity as derived by the sensor, characterized in that connected to the output of the sensor (20, 22) is a clocked analog integrator (26), which in analog fashion integrates the measurement signal, in accordance with a first, adjustable timing code with relatively short code intervals (a) at least once in each of these short code intervals, via a certain integration interval (c) of adjustable chronological length;

that connected to the output of the integrator (26) is an analog/digital converter (28), which digitizes the analog-integrated measurement values of the integrator each at the end of the individual integration intervals (c);

that connected to the output of the analog/digital converter (28) is an averaging addition element (30), which arithmetically adds and averages the digitized measurement values of a plurality successive code intervals (a) of the first timing code in accordance with a second, adjustable timing code with comparatively longer code intervals (b) in each of these longer code intervals; and that connected to the output of the addition element (30) is a memory element (32) for storing successive, arithmetically added, averaged measurement samples in memory in a manner that can be chronologically ordered and called up.

13. The device of claim 12, characterized in that the integrator (26), the analog/digital converter (28), and the addition element (30) are connected to at least one adjustable clock generator (36).

14. The device of claim 12, characterized by a microprocessor (36) that generates both the first and second timing codes and the integration intervals and controls the individual elements of the device.

15. The device of claims 12, characterized in that the memory element (32) is embodied as a shift register.

16. The device of claim 12, characterized by a random generator (38), connected to a clock generator or microprocessor (36), for randomly controlled shifting of the integration intervals.

* * * * *